US006945662B2

(12) United States Patent
Diehr

(10) Patent No.: US 6,945,662 B2
(45) Date of Patent: Sep. 20, 2005

(54) CONTAINER INSPECTION MACHINE

(75) Inventor: Richard D. Diehr, Horseheads, NY (US)

(73) Assignee: Emhart Glass S.A., Cham (CH)

( * ) Notice: Subject to any disclaimer, the term of this patent is extended or adjusted under 35 U.S.C. 154(b) by 80 days.

(21) Appl. No.: 10/610,232

(22) Filed: Jun. 30, 2003

(65) Prior Publication Data

US 2004/0264165 A1 Dec. 30, 2004

(51) Int. Cl.⁷ .................... A61G 13/00; G01N 21/00
(52) U.S. Cl. .................. 362/33; 362/253; 326/239.4
(58) Field of Search .................... 362/33, 253, 84; 356/239.1, 239.4, 239.8

(56) References Cited

U.S. PATENT DOCUMENTS

| 4,021,122 A | * | 5/1977 | Krenmayr | 356/239.4 |
|---|---|---|---|---|
| 5,095,204 A | * | 3/1992 | Novini | 250/223 B |
| 6,012,344 A | * | 1/2000 | Halbo | 73/865.8 |
| 6,122,048 A | * | 9/2000 | Cochran et al. | 356/239.4 |
| 6,452,156 B2 | * | 9/2002 | Lindner | 250/223 B |

* cited by examiner

Primary Examiner—Ali Alavi
(74) Attorney, Agent, or Firm—Spencer T. Smith

(57) ABSTRACT

The man-machine screen interface can be switched to one of a plurality of back lights so that an operator can define any one of these back lights on the man-machine screen interface as a desired back light for inspecting a transparent container.

2 Claims, 3 Drawing Sheets

CONTAINER INSPECTION MACHINE

The present invention relates to machines which inspect bottles for defects.

BACKGROUND OF THE INVENTION

Glass bottles are formed in a process which can produce defects which make the bottle unacceptable. For example, the side wall of a bottle may include a "stone" which makes the bottle visually unacceptable or the bottle may have a "bird swing" which could break off and become part of the contents of the bottle.

One of the crudest ways that a bottle is inspected is for an operator to remove a bottle from a conveyer and look through the bottle at a light source within sight of the operator (a ceiling light for example). Operators believe that certain defects can be identified in this manner. Inspection equipment improves on this process and conventionally defines a light source which is part of an inspection station within a piece of inspection equipment. The inspection may be of a very simple form with an inspector watching bottles as they pass in front of a large opaque light screen but this light source may be inconvenient for the operator.

A camera may look through a bottle which is backlighted by this light source and an inspection algorithm attempts to identify a defect. The back light may have a great variety of forms but defines either a diffuse back light or a patterned back light. One form of patterned back light is a black and white stripe such as would be defined by a light intensity having an intensity which varies linearly as a sine function.

OBJECT OF THE INVENTION

It is an object of the present invention to provide the operator with a patterned or diffuse light source at an inspection machine that can back light a bottle to provide the operator with an improved way of carrying out a crude inspection of a bottle held in his hand.

Other objects and advantages of the present invention will become apparent from the following portion of this specification and from the accompanying drawings which illustrate, in accordance with the mandate of the patent statutes, a presently preferred embodiment incorporating the principles of the invention.

BRIEF DESCRIPTION OF THE PREFERRED EMBODIMENT

Figure 1:
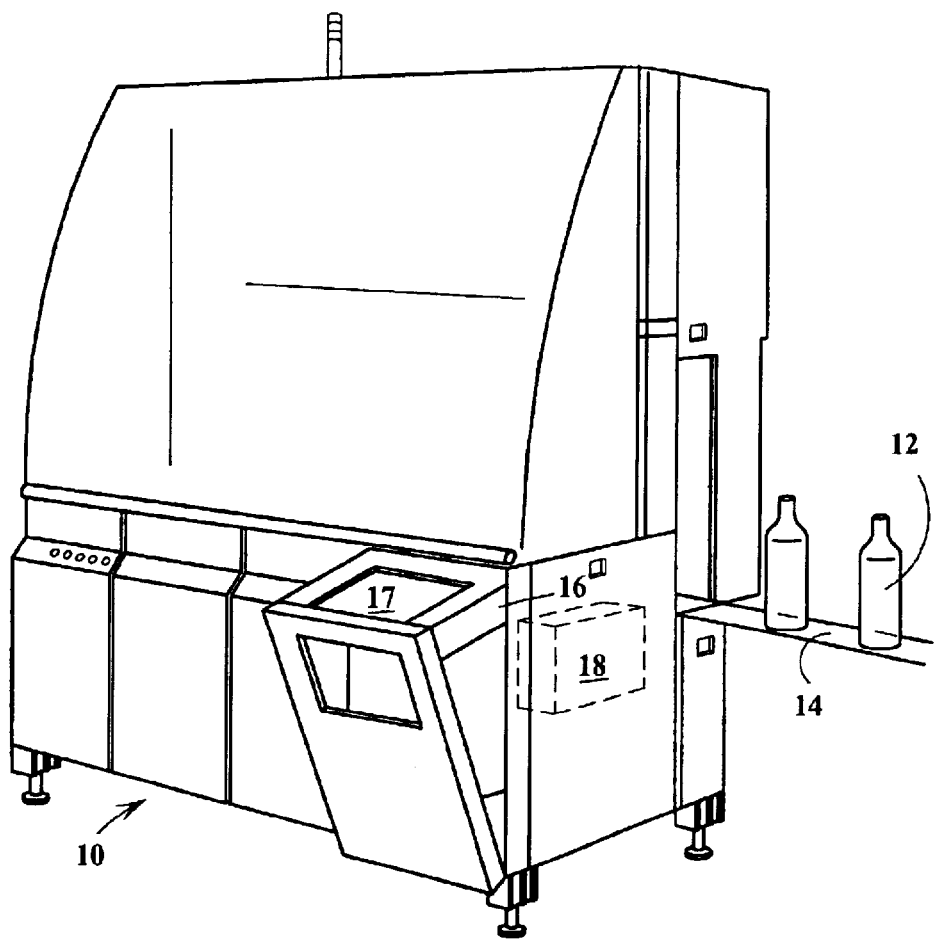
FIG. 1 is a schematic oblique view of an inspection machine for inspecting bottles which includes a controller and a screen which functions as a man-machine interface.

FIG. 1 is a schematic showing of an inspection machine 10 which inspects a row of bottles 12 conveyed through the machine on a conveyor 14. Any of a variety of inspections can be carried out by the machine. For example the bottle can be inspected to determine the mold information that the producer puts on the bottle so that defects can be correlated with the mold in which the bottle was made. The opening of the bottle can be inspected to make sure that the I.D. (inner diameter) and O.D. (outer diameter) are acceptable. The sides of the bottle can be inspected to make sure that they are vertical and have no defects such as thin or thick spots.

The inspection machine has an operator console 16 which includes a man-machine interface in the form of a touch screen 17. With this screen, the operator can perform numerous functions relating to the operation of the machine. The screen is controlled by a computer 18 and the screen could be a LCD (liquid crystal diode) screen.

Figure 2:
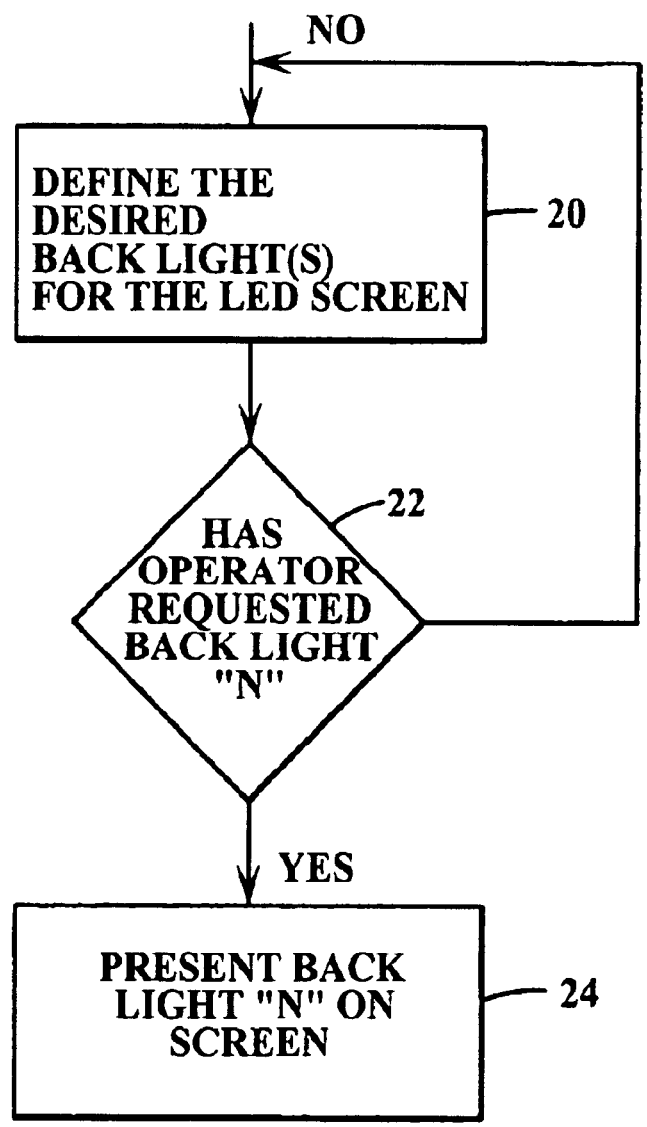
FIG. 2 is a logic diagram illustrating how the screen can be operated as a light source.

Backlights can be diffuse (white) or patterned. One common pattern is a black and white stripe where the light intensity moving in a selected direction, varies as a sinusoidal function between black and white and repeats every ¼ inch (for example). Referring to FIG. 2, the first thing that is done is to Define The Desired Back Lights For The LCD Screen. There could be any number "N". When the query "Has Operator Requested Backlight "N" 22 is answered in the affirmative, the control will Present Backlight "N" On Screen" 24.

Figure 3:
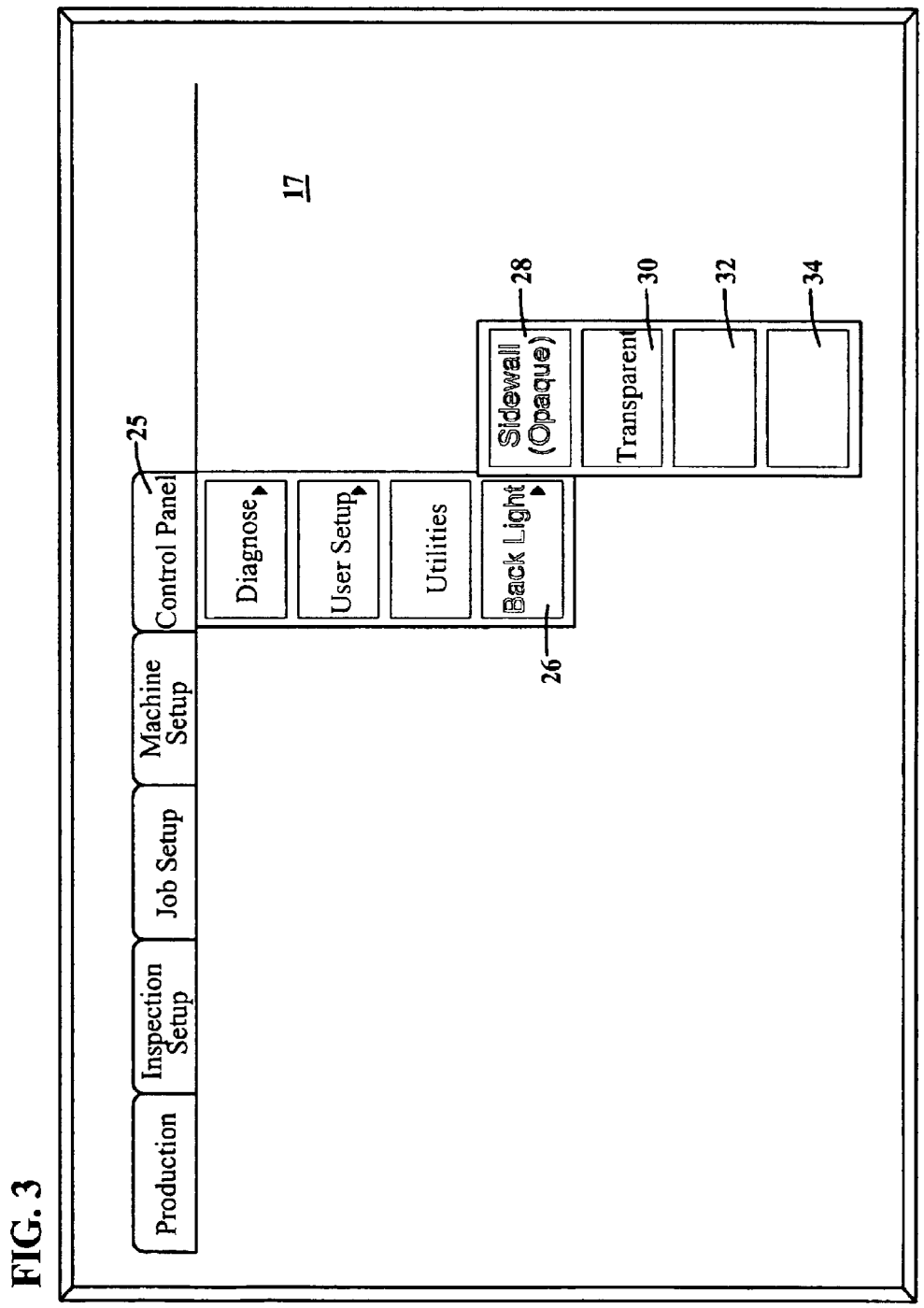
FIG. 3 is a front view of the screen illustrating how an operator would define a desired light source that he could use for inspection purposes.

FIG. 3 shows the screen 17 as it would be used by an operator to define a desired backlight on the screen. The Control Panel tab 25 is operated which presents a menu including the option "Back Light" 26. When this menu item is operated a submenu including Sidewall (Opaque) 28 (a brightness pattern varying repeatedly along an axis in a sinusoidal manner between black and white), Transparent 30 (white light), with two other submenu locations 32,34 for additional back light choices. The operator touches the desired back light and the control illuminates the screen accordingly. The operator now has defined a convenient light source which he can use to back light a bottle that he has removed from the conveyor and would like to inspect.

What is claimed is:

1. A machine for inspecting a transparent container comprising a control system including a control and a man-machine screen interface, said control comprising means for defining a plurality of back lights which can be defined on the man-machine screen interface for use by an operator to inspect a transparent container, said man-machine screen interface including menu means for identifying a corresponding plurality of discrete back lights which can be presented on the man-machine screen interface whereby an operator can define any one of the plurality of back lights on the man-machine screen interface so that the operator can perform an inspection of a transparent container with that back light.

2. A machine for inspecting a transparent container according to claim 1 wherein the discrete back lights which can be defined on the man-machine screen interface include sidewall and transparent.

* * * * *